United States Patent
Wuzik et al.

(10) Patent No.: US 6,525,512 B2
(45) Date of Patent: Feb. 25, 2003

(54) MEDICALLY IMPLANTABLE ENERGY STORAGE SYSTEM HAVING SAFE RECHARGING CAPABILITIES

(75) Inventors: Martin Wuzik, Ismaning (DE); Hans Leysieffer, Taufkirchen (DE)

(73) Assignee: Cochlear Limited, Lane Cove (AU)

( * ) Notice: Subject to any disclaimer, the term of this patent is extended or adjusted under 35 U.S.C. 154(b) by 0 days.

(21) Appl. No.: 09/824,242

(22) Filed: Apr. 3, 2001

(65) Prior Publication Data

US 2001/0026146 A1 Oct. 4, 2001

(30) Foreign Application Priority Data

Apr. 3, 2000 (DE) .......................... 100 16 519

(51) Int. Cl.⁷ .............................. H02J 7/00; A61H 1/10
(52) U.S. Cl. ........................... 320/122; 607/55; 607/61
(58) Field of Search ................ 607/33, 61, 55; 320/137, 136, 122

(56) References Cited

U.S. PATENT DOCUMENTS

| | | | |
|---|---|---|---|
| 4,658,358 A | * 4/1987 | Leach et al. | 73/865.1 |
| 5,411,537 A | 5/1995 | Munshi et al. | 607/33 |
| 5,690,693 A | * 11/1997 | Wang et al. | 607/61 |
| 5,702,431 A | 12/1997 | Wang et al. | 607/61 |
| 5,713,939 A | 2/1998 | Nedungadi et al. | 607/33 |
| 6,100,664 A | * 8/2000 | Oglesbee et al. | 320/125 |
| 6,137,265 A | * 10/2000 | Cummings et al. | 320/133 |
| 6,154,677 A | 11/2000 | Leysieffer | 607/61 |
| 6,358,281 B1 | * 3/2002 | Berrang et al. | 607/57 |

\* cited by examiner

*Primary Examiner*—Edward H. Tso
*Assistant Examiner*—Pia Tibbits
(74) *Attorney, Agent, or Firm*—Nixon Peabody LLP; David S. Safran

(57) ABSTRACT

An implantable energy storage system for a medical implant, which is provided with a rechargeable storage for electric energy and a unit for controlling the charging process. The system includes a monitoring unit which is independent of the control unit and which senses the storage voltage independently of the control unit and is designed such that it assumes control of the charging path when the sensed storage voltage lies outside a predetermined range. Furthermore, a corresponding process for operating the implantable energy storage system is provided.

21 Claims, 1 Drawing Sheet

MEDICALLY IMPLANTABLE ENERGY STORAGE SYSTEM HAVING SAFE RECHARGING CAPABILITIES

BACKGROUND OF THE INVENTION

1. Field of the Invention

The present invention is directed to an implantable energy storage system for a medical implant and includes a rechargeable storage for electrical energy and a unit for controlling the charging process. In addition, the present invention is directed to a process for operating such an energy storage system.

2. Description of Related Art

Energy storage systems of the afore-mentioned type and associated operating processes are disclosed in U.S. Pat. No. 5,411,537, U.S. Pat. No. 5,702,431, U.S. Pat. No. 5,713,939 and U.S. Pat. No. 6,154,677. Conventionally, implantable energy storage systems are recharged transcutaneously via an inductive path by means of an external charging device. The charging operation is conventionally controlled by way of a control unit which measures the charging current and the voltage of the storage and converts the measured values into corresponding control pulses for a switch provided in the charging circuit, with a suitable charging program being used.

When the energy storage is in operation, two undesirable operating states can occur, first, overcharging of the battery can occur if the charging process is not terminated at the proper time; which leads to gas evolution with subsequent destruction of the storage. Second, the storage voltage, when charging of the storage is not done on time, can drop to values which are below a minimum operating voltage which is necessary for defined operation or optionally for limited function of the implant which is to be supplied by the energy storage. In the latter case, under certain circumstances, the storage voltage can drop to such an extent that even supply of sufficient voltage to the implant-side electronics no longer ensures control of the charging process. Often, the controller includes a microprocessor system in which, in the case of undervoltage, wrong logic operations can occur or contents of volatile memories can be lost. Thus, in the case of undervoltage, in these systems proper charge control is no longer ensured, which can lead to the charging path being switched to high resistance by a microprocessor malfunction when entering the undervoltage range, whereby charging of the storage is permanently prevented.

Even if such a blockage of the charging path does not occur, a different problem can arise when the storage is being recharged. This results from the fact that, in power-saving circuits, Pierce oscillators are often used which are known to be difficult to start. To enable reliable transient oscillation of the oscillator, the power supply voltage must rise as quickly as possible from the undervoltage range. However, when the rechargeable storage is being charged, the voltage rises relatively slowly; this can lead to the oscillator not being able to start under certain circumstances, which prevents the microprocessor from being started up again.

SUMMARY OF THE INVENTION

A primary object of the present invention is to provide an implantable energy storage system for a medical implant, and a process for its operation, with safe operation being guaranteed at any time and safe recharging of the energy storage being possible even when the storage has been discharged, at least to such an extent that the storage voltage has dropped below the normal voltage range for the control unit.

This as well as other objects are achieved in accordance with the present invention by an implantable energy storage system for a medical implant and includes a rechargeable storage for electrical energy and a unit for controlling charging of the energy storage system, wherein a monitoring unit is provided which is independent of the control unit. The monitoring unit senses the storage voltage independently of the control unit and is made so as to assume control of the charging path when the sensed storage voltage lies outside of a predetermined range.

This as well as other objects are achieved in accordance with the present invention by a process for operating an implantable energy storage system for a medical implant including a rechargeable storage for electrical energy, wherein during normal operation the charging process is controlled by way of a control unit, wherein the storage voltage is sensed independently of the control unit by means of a monitoring unit which is independent of the control unit, and wherein the monitoring unit assumes control of the charging path when the sensed storage voltage lies outside a predetermined range. In this approach, in accordance with the present invention, it is advantageous that by providing a monitoring unit which is independent of the control unit, even when the control unit has failed, for example, due to very low storage voltage when the storage has been substantially discharged, proper charging control is possible, and especially the rechargeability of the storage can be ensured at any time by preventing blockage of the charging path due to malfunction of the control unit caused by undervoltage.

In a preferred embodiment of the invention, the control unit controls the charging process via a controllable resistance in the charging path, the resistance being made conductive by the monitoring unit when the sensed storage voltage falls below a predetermined first lower threshold value. Preferably, the control unit contains a microprocessor which, via a first switch, is supplied with power from the storage, the monitoring unit being chosen such that when the sensed storage voltage falls below a predetermined second lower threshold which preferably corresponds to the first lower threshold, the control unit cuts off the microprocessor system from the power supply by the storage by opening the first switch. In this way, the microprocessor is prevented from operating in an undervoltage range in which malfunctions can occur. In addition, in this way the power drain from the storage can be reduced; this increases the time interval to complete discharge of the storage and thus reduces the danger of complete discharge.

Preferably, the monitoring unit is made such that when the sensed storage voltage exceeds a predetermined first upper threshold, by closing the first switch it connects the microprocessor system to the power supply by the storage and transfers control of the first switch to the microprocessor. In this way, the power supply voltage is "suddenly" turned on and thus a very steep rising edge is realized; this facilitates the stimulation of oscillations of an oscillator associated to the microprocessor. In addition, in this way, hysteresis can be set so that the microprocessor is restarted only when a fully sufficient storage voltage is reached. Furthermore, the monitoring unit is preferably designed such that, when the storage voltage exceeds a predetermined maximum value, overcharging of the storage independently of the control system is prevented by the monitoring unit switching the charging path such that charging current is prevented from continuing to flow to the storage.

A second preferred embodiment includes a bypass mechanism which is externally actuated to bypass the controllable resistor at least when the energy storage has been completely discharged. The bypass mechanism can be formed by a magnetically actuateable switch or by a diode which is poled in reverse direction. Even when the storage is completely discharged and even when the monitoring means can no longer operate, the bypass mechanism ensures that the storage can again be supplied with charging current.

These and further objects, features and advantages of the present invention will become apparent from the following description when taken in connection with the accompanying drawing which, for purposes of illustration only, shows an embodiment in accordance with the present invention.

BRIEF DESCRIPTION OF THE DRAWINGS

The sole FIGURE is a block diagram of an implantable storage system for a medical implant in accordance with the present invention.

DETAILED DESCRIPTION OF THE INVENTION

Figure 1:
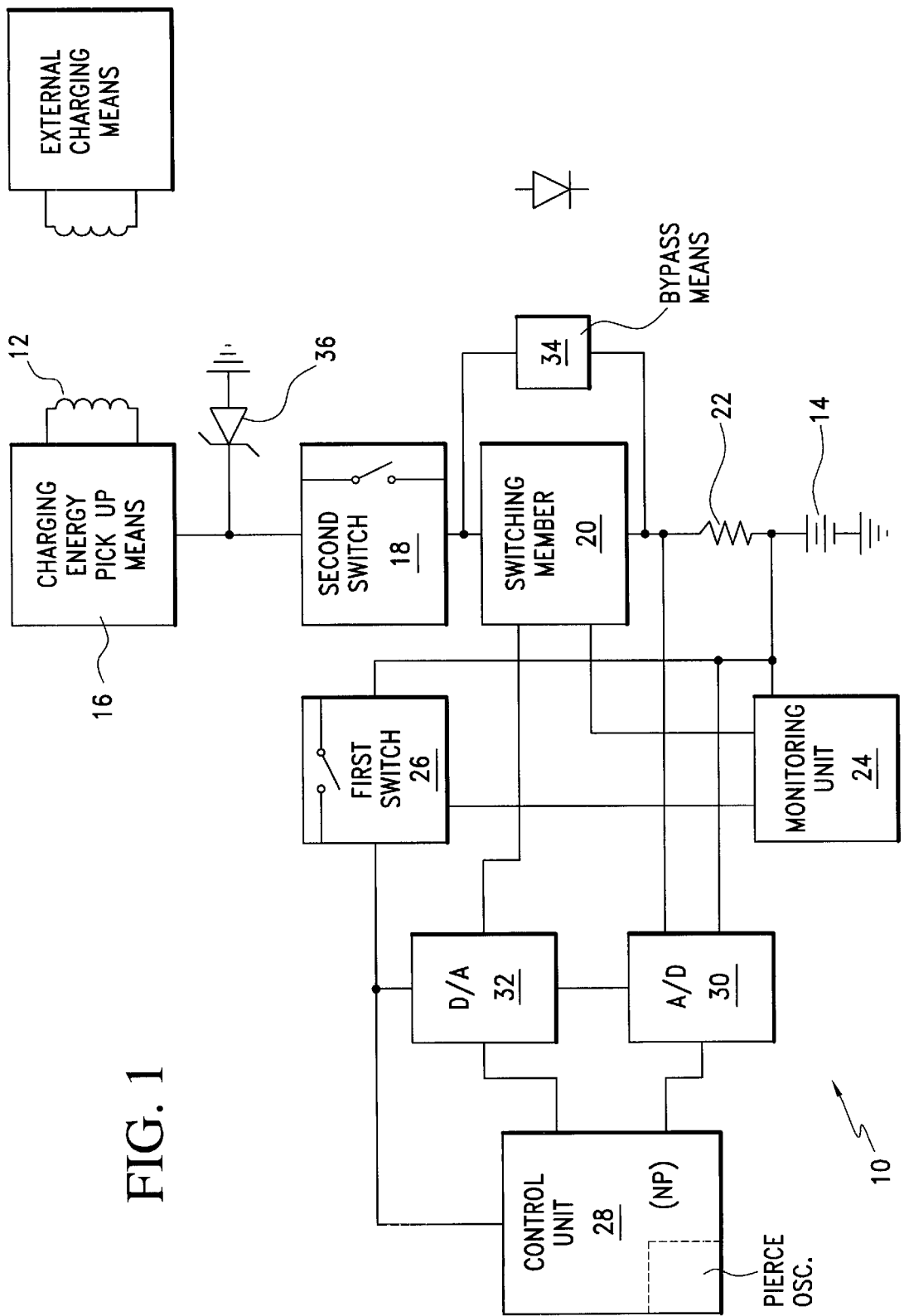

The sole FIGURE schematically shows the wiring of the essential elements of an implantable storage system 10 which is used as power supply for a medical implant which can be, for example, a fully implantable hearing system for direct mechanical stimulation of the middle ear or inner ear or electrical stimulation of the inner ear. A charging coil 12 is used to pick up electrical energy which has been inductively transmitted transcutaneously by an external charging device (not shown) and to feed power into the charging path of a rechargeable energy storage 14, such as a NiMH battery. The voltage induced in the charging coil 2 by the external charging device is rectified and conditioned in a unit 16. A Zener diode 36 protects the electronic components which are at the charging voltage potential against excessive charging voltage.

The charging current flows to the battery 14 through a mechanical switch 18 which is closed in normal operation, through a control and switching element 20, such as a FET, and which acts as a controllable resistor in the charging current path, and through a shunt resistor 22. A monitoring unit 24 is connected directly to the battery 14 and is used to sense and monitor the battery voltage. On the output side, the monitoring unit 24 is connected to the control and switching element 20 and also to the switch 26, by which a microprocessor system 28 is connected to the battery 14 which acts as voltage supply. The microprocessor system 28 is clocked preferably by a Pierce oscillator (not shown). An A/D converter 30 is used to measure the voltage of the battery 14 and the voltage drop across the shunt resistor 22, in which manner the two most important parameters when the battery 14 is being charged, specifically the battery voltage and the charging current, can be measured.

The A/D converter 30 outputs these values as an input signal to the microprocessor system 28 which, depending on the sensed battery voltage and the sensed charging current controls, via a D/A converter 32, the control/switching element 20, and thus the charging current or the charging voltage, respectively, in conformity with a predetermined charging strategy. In particular, a monitoring function is implemented in a conventional manner. This monitoring function provides for the charging process to be terminated after a predetermined charging end criterion being reached by switching the control/switching element 20 to high resistance.

To prevent excess discharging of the battery 14 in operation, the energy storage system 10 is conventionally provided with a function which timely warns the implant wearer of discharge of the battery 14 in order to encourage him to undertake a charging process. If recharging does not take place because, for example, the implant wearer is prevented from doing so, the battery voltage can drop below the allowable lower limit.

As soon as the monitoring unit 24 ascertains that the sensed battery voltage has fallen below a predetermined lower threshold, the monitoring unit 24, on the one hand, turns off the microprocessor 28 by opening the switch 26 by interrupting the voltage supply thereof This ensures that the microprocessor 28 is not operated at power supply voltages which are so low that the microprocessor 28 can execute incorrect logic operations or can lose the contents of volatile memories. This is ensured by correspondingly selecting the lower voltage limit. On the other hand, the monitoring unit 24 sets the control/switching element 20 into a conductive state when the voltage falls below the lower voltage limit to ensure that charging of the battery 14 is also possible at any time in the undervoltage range and blockage of the charging path by malfunction of the microprocessor 28 is prevented. As an additional effect, turning off the microprocessor 28 results in the power consumption of the electronics being reduced to the power consumption of the monitoring unit 24 which is only some 100 nA in practice. This has the benefit that the battery 14 is less loaded, and thus, the time interval to complete discharge of the battery 14 is lengthened; this reduces the risk of complete discharge.

In a charging process which is undertaken in the undervoltage range, the voltage of the battery 14 gradually increases. After the battery voltage has exceeded the stipulated lower voltage threshold of the monitoring unit 24 by the value of hysteresis, the monitoring unit 24 again turns on the microprocessor system 28 by closing the switch 26, by which the microprocessor system begins to control and monitor the charging process in the above described manner. In this way, the control of the control/switching element 20 is transferred from the monitoring unit 24 to the microprocessor system 28. By suddenly turning on the power supply voltage by closing the switch 26, a steep voltage rise is accomplished which reliably ensures stimulation of oscillations of the Pierce oscillator of the microprocessor system 28.

Furthermore, the monitoring unit 24 is designed such that, when the sensed battery voltage exceeds a predetermined maximum value, the control/switching element 20 is switched into a non-conductive state to prevent overcharging of the battery 14 even when the microprocessor system 28 due to an error does not terminate the charging process after reaching the stipulated charging end criterion. The mechanical switch 18 is designed in a conventional manner such that it responds to mechanical expansion of the battery 14 as occurs in case of excess gas evolution which accompanies overcharging, and interrupts the charging path or prevents reception of charging energy to prevent further charging of the battery 14. In this way, three independent monitoring circuits are implemented in the described storage system 10 which monitoring circuits terminate the charging of the battery at the proper time to prevent damage. It is primarily the microprocessor system 28 which terminates the charging process when a stipulated charging end criterion is reached. Independent therefrom, the monitoring unit 24 terminates the charging process when the battery voltage sensed by it independently of the microprocessor system 28 exceeds a stipulated maximum value. Finally, when the first two monitoring circuits fail the mechanical switch 18 timely terminates the charging process independently of the electronics such that damage of the battery 14 and hazard to the implant carrier are reliably prevented.

Furthermore, the monitoring unit 24, independently of the microprocessor system 28, detects threatening excess discharging of the battery 14, malfunctions of the microprocessor system 28 which may result therefrom are prevented by turning off the microprocessor system. Furthermore, in this case, the monitoring unit 24 assumes control of the charging path, whereby, independently of the microprocessor system 28, in the undervoltage range, it is always ensured that the charging path is conductive so that recharging of the battery 14 is possible at any time. Besides, by suddenly again turning on the power supply voltage of the microprocessor 28 by closing of the switch 26 by means of the monitoring unit 24, start-up problems of the Pierce oscillator of the microprocessor system 28 can be prevented.

A bypass means 34 is connected in parallel to the control/switching element 20 and can be actuated externally, i.e. from outside of the body, in order to bypass or short-circuit the control/switching element 20. The bypass means 34 is provided for the case in which the storage 14 is discharged such that the storage voltage has dropped so far that it is no longer sufficient for proper operation of the monitoring unit 24. Here the case can arise that the control/switching element 20 assumes a resistance which is so high that it does not enable charging of the storage 14 via the normal charging path. In this case, by actuating the bypass means 34 it is possible to intervene from the outside to bypass the control/switching element 20 and thus enable reliable charging of the storage 20 even in case of an extreme undervoltage or complete discharge.

The bypass means 34 may include a mechanical switch which is closed by way of an external magnet (Reed switch), and the magnet can preferably be integrated into the external charging device. In this case, when the charging device is held on the skin of the implant wearer, the switch 34 is closed and charging is possible via the current path through switch 34. But as soon as the storage voltage is sufficient again for reliable operation of the monitoring unit 24, the switch 34 should be opened again by removing the magnet in order to re-activate the above described normal charging function and especially to prevent overcharging.

In an alternative embodiment, the bypass means 34 can also be formed by a diode which is poled in the reverse direction, for example a Zener diode. The reverse voltage of the diode is dimensioned such that it is above the charging voltages which occur in the normal charging mode and thus does not influence the normal charging process, but lies below the reverse voltage of the protective diode 36. In an emergency, i.e., when the storage voltage is no longer sufficient for operation of the monitoring unit 24, a special external emergency charging device is used at the start of recharging which external emergency charging device differs from the external charging device which is used for the normal charging process essentially in that it provides for a charging voltage to be produced which is much higher than in a normal charging process and above the reverse voltage of the bridging diode 34, but below the reverse voltage of the protective diode 36. In this way, bridging of the control/switching element 20 is achieved by the emergency charging device.

Instead of using a special emergency charging device, the normal charging device can also be provided with a switchable emergency charging mode. However, when a storage voltage which again is sufficient for reliable operation of the monitoring unit 24 is reached, the emergency charging mode should be terminated to again block the bridging diode 34 and thus to re-activate the normal charging function and especially to prevent overcharging. By means of the bypass unit 34, it is thus ensured that recharging by external activation is possible even when the storage 14 is completely discharged.

We claim:

1. An implantable energy storage system for a medical implant, said implantable energy storage system comprising:
    a rechargeable storage device that stores electric energy;
    a control unit that controls charging of said implantable energy storage system;
    a monitoring unit that senses battery voltage independently of the control unit, said monitoring unit assuming control of a charging path when a sensed battery voltage lies outside of a predetermined range;
    wherein said monitoring unit operates independent of said control unit.

2. The storage system of claim 1, wherein the monitoring unit is adapted to switch the charging path such that a charging current can be supplied to said rechargeable storage device when the sensed battery voltage falls below a predetermined first lower threshold.

3. The storage system of claim 2, wherein said control unit regulates a switching element located in the charging path and controls the charging process, said a switching element being electrically charged by said monitoring unit when the battery voltage sensed by said monitoring unit falls below said predetermined first lower threshold.

4. The storage system of claim 3, wherein said switching element comprises a controllable resistance.

5. The storage system of claim 4, wherein said control unit further comprises a microprocessor system which is supplied with voltage by said rechargeable storage device via a first switch; and wherein said monitoring unit cuts off the microprocessor system from supplying voltage from said rechargeable storage device by opening a second switch when the sensed battery voltage falls below a predetermined second lower threshold.

6. The storage system as claimed in claim 5, wherein said first lower threshold and said second lower threshold are identical.

7. The storage system of claim 5, wherein said monitoring unit electrically connects said microprocessor system, by closing said first switch, to the voltage supply in said rechargeable storage device and transfers control of said switching element to said microprocessor system when the sensed battery voltage exceeds said predetermined first upper threshold.

8. The storage system as claimed in claim 5, further including a Pierce oscillator for providing clock signals to said microprocessor system.

9. The storage system of claim 3, wherein said control unit further comprises sensing means for sensing a battery voltage and a current in a charging circuit, and for controlling the switching element according to a charging program as a function of the sensed values.

10. The storage system as claimed in claim 4, wherein said controllable resistance comprises a FET.

11. The storage system of claim 4, further comprising bypass means for bypassing said controllable resistance at least when the rechargeable storage device has been completely discharged, said bypass means being externally activated.

12. The storage system as claimed in claim 11, wherein said bypass means comprises a magnetically-actuatable switch.

13. The storage system as claimed in claim 11, wherein said bypass means comprises a diode which is poled in a reverse direction.

14. The storage system as claimed in claim 13, wherein said control unit and said monitoring means further comprise a protective diode having a reverse voltage which is greater than a reverse voltage of said diode for said bypass means.

15. The storage system of claim 1, wherein said monitoring unit switches the charging path such that charging current is prevented from flowing to said rechargeable storage device when the battery voltage exceeds a predetermined maximum value.

16. The storage system of claim 15, wherein said control unit controls a switching element positioned in the charging path for controlling the charging process, said switching element being electrically charged by said monitoring unit when the battery voltage sensed by said monitoring unit falls below a predetermined first lower threshold, and wherein said monitoring unit makes said actuator non-conductive when the battery voltage exceeds a predetermined maximum value.

17. The storage system of claim 1, further comprising a second switch for either decoupling said rechargeable storage device from a charging current source or preventing reception of charging energy to said rechargeable storage device when said rechargeable storage device is overcharged.

18. The storage system of claim 17, wherein said second switch either interrupts the charging current path or prevents reception of charging energy to said rechargeable storage device when said rechargeable storage device is overcharged.

19. The storage system as claimed in claim 1, further comprising means for picking up charging energy which is inductively transmitted transcutaneously from an external source and for conditioning the charging energy to be fed into the charging current path.

20. The storage system as claimed in claim 1, wherein the medical implant is a fully implantable hearing system.

21. A process for operating an implantable energy storage system for a medical implant, said process comprising the steps of:

providing a rechargeable storage device that stores electric energy;

providing a control unit;

providing a monitoring unit which operates independent of said control unit, controlling a charging process of the implantable energy storage system via said control unit; and sensing a battery voltage in said rechargeable storage device via said monitoring unit;

wherein said monitoring unit assumes control of a charging path of said rechargeable storage device when the sensed battery voltage lies outside a predetermined range.

* * * * *